(12) United States Patent
Kume et al.

(10) Patent No.: US 8,778,404 B2
(45) Date of Patent: *Jul. 15, 2014

(54) NUTRITIONAL COMPOSITIONS

(75) Inventors: Hisae Kume, Kanagawa (JP); Makoto Yamaguchi, Kanagawa (JP); Kenji Mizumoto, Kanagawa (JP); Hajime Sasaki, Kanagawa (JP)

(73) Assignee: Meiji Co., Ltd., Tokyo (JP)

( * ) Notice: Subject to any disclaimer, the term of this patent is extended or adjusted under 35 U.S.C. 154(b) by 751 days.

This patent is subject to a terminal disclaimer.

(21) Appl. No.: 12/475,482

(22) Filed: May 30, 2009

(65) Prior Publication Data

US 2009/0233865 A1     Sep. 17, 2009

Related U.S. Application Data

(63) Continuation of application No. 10/535,585, filed as application No. PCT/JP03/14918 on Nov. 21, 2003, now Pat. No. 7,563,458.

(30) Foreign Application Priority Data

Nov. 22, 2002  (JP) ................................. 2002-339948

(51) Int. Cl.
    *A61K 35/20*  (2006.01)

(52) U.S. Cl.
    USPC ............. 424/535; 514/5.5; 514/5.6; 514/12.2

(58) Field of Classification Search
    None
    See application file for complete search history.

(56) References Cited

U.S. PATENT DOCUMENTS

| | | | |
|---|---|---|---|
| 4,499,076 A | 2/1985 | Ohashi et al. | |
| 4,600,588 A | 7/1986 | Ernster | |
| 5,198,250 A | 3/1993 | Brillhart et al. | |
| 5,691,165 A | 11/1997 | Nielsen et al. | |
| 5,709,888 A | 1/1998 | Gil et al. | |
| 5,714,472 A | 2/1998 | Gray et al. | |
| 5,780,439 A | 7/1998 | Mendy et al. | |
| 5,993,221 A | 11/1999 | Bistrian | |
| 6,733,770 B1 | 5/2004 | Garcia-Rodenas et al. | |
| 6,737,076 B2 | 5/2004 | Fritsche et al. | |
| 6,830,766 B2 | 12/2004 | McCabe | |
| 6,998,259 B1 | 2/2006 | Davis et al. | |
| 2005/0002988 A1 | 1/2005 | Mizumoto et al. | |

FOREIGN PATENT DOCUMENTS

| | | |
|---|---|---|
| JP | 5-015339 | 1/1993 |
| JP | 08-056612 A | 3/1996 |
| JP | 3167723 | 5/2001 |
| JP | 2001-233783 A | 8/2001 |
| JP | 2001-247474 | 9/2001 |
| JP | 2002-226394 | 8/2002 |
| JP | 2002-255824 | 9/2002 |
| JP | 2002-538797 A | 11/2002 |
| WO | WO 02/19837 | 3/2002 |

OTHER PUBLICATIONS

Grimm, H. et al. "Regulatory Potential of N-3 Fatty Acids in Immunological and Inflammatory Processes" *British Journal of Nutrition*, 2002, pp. S59-S67, vol. 87, Suppl. 1.
Kawai, K., et al. "Usefulness of Palatinose as a Caloric Sweetener for Diabetic Patients" *Horm. Metabol. Res.*, 1989, pp. 338-340, vol. 21.
Khalfoun, B. et al. "Docosahexaenoic and Eicosapentaenoic Acids Inhibit In Vitro Human Endothelial Cell Production of Interleukin-6" *Adv. Exp. Med. Biol.*, 1997, pp. 589-597, vol. 400B.
Mayer, K. et al. "Parenteral Nutrition with N-3 Lipids in Sepsis" *British Journal of Nutrition*, 2002, pp. S69-S75, vol. 87, Suppl. 1.
Siegenthaler, E.J., "The Potential Value of Cultured Dairy Products for Child Nutrition" *Arch. Latinoam. Nutr.*, Jun. 1983, pp. 247-256, vol. 33, No. 2.
WPI Accession No. AN 2003-032691, 2003, Derwent abstract for JP 2002226394A.

*Primary Examiner* — Satyendra Singh
(74) *Attorney, Agent, or Firm* — Saliwanchik, Lloyd & Eisenschenk (57) ABSTRACT

The present inventors discovered that the onset of galactosamine hepatopathy is suppressed by nutritional compositions comprising as essential ingredients: whey protein hydrolysates; lecithin and oils and fats high in oleic acid, which are able to improve the lipid metabolism; and palatinose having an insulin-sparing effect. Furthermore, the whey protein hydrolysate included in the nutritional compositions was found to suppress endotoxin-induced TNF-a and interleukin 6 (IL-6) production in macrophages.

18 Claims, 9 Drawing Sheets

NUTRITIONAL COMPOSITIONS

CROSS-REFERENCE TO A RELATED APPLICATION

This application is a continuation application of U.S. Ser. No. 10/535,585, filed May 18, 2005; which issued as U.S. Pat. No. 7,563,458 on Jul. 21, 2009, which is a National Stage Application of International Application Number PCT/JP2003/014918, filed Nov. 21, 2003; which claims priority to Japanese Application No. 2002-339948, filed Nov. 22, 2002; all of which are incorporated herein by reference in their entirety.

TECHNICAL FIELD

The present invention relates to nutritional compositions useful for nutritional management and therapy of liver disease patients. The present invention also relates to nutritional compositions useful for metabolic and nutritional management in patients experiencing invasive stresses such as surgery, infections and scalds. Furthermore, the present invention relates to nutritional compositions useful for pathological improvement of patients with inflammatory diseases.

BACKGROUND ART

In the nutritional pathology of liver disease, with regard to the carbohydrate metabolism, abnormal glucose tolerance is frequently observed generally due to changes in glycolytic enzyme activity and reduced insulin sensitivity at the periphery. This is especially the case in liver cirrhosis, where energy consumption is enhanced and the availability of carbohydrates as an energy substrate is decreased. Observations of the protein metabolism in hepatitis and liver cirrhosis show an imbalance of plasma amino acids (a decrease in the branched chain amino acid/aromatic amino acid ratio (the Fischer ratio)), enhanced protein catabolism, hyperammonemia, and hypoproteinemia due to a negative nitrogen balance. Furthermore, with regard to the lipid metabolism a decrease in polysaturated fatty acids and lipid-soluble vitamins is seen.

Liver cirrhosis includes compensated and decompensated cirrhosis, which differ in pathology as well as in their metabolic and nutritional management. Compensated cirrhosis can be managed in much the same way as chronic hepatitis. However, decompensated cirrhosis is a state of chronic liver failure, and since protein catabolism is enhanced, excess protein administration may lead to hyperammonemia. Oral administration of the branched chain amino acids (BCAAS) valine, leucine, and isoleucine can suppress protein catabolism in peripheral tissues, and enhance protein synthesis in the liver. Furthermore, BCAAs metabolized in muscles form alanine, which activates glucogenesis (the glucose-alanine cycle) in the liver, and improves the efficiency of carbohydrates as an energy substrate. Therefore, PCAA preparations (Hepan ED®, Aminoleban EN®: 50 to 150 g/day) are used to supplement a lack of energy in skeletal muscles.

On the other hand, when a living body experiences something excessively invasive such as surgery, infection, or scalds, the production of local and systemic inflammatory mediators is enhanced. Cytokines in particular are important mediators, inducing a variety of reactions in the circulatory, endocrine, immune and metabolic systems, etc.

In general, metabolic reactions during invasion characteristically include enhanced proteolysis of body proteins, especially skeletal muscles; production of glycerol and fatty acids due to enhanced lipolysis; and gluconeogenesis, acute-phase protein production and albumin production in the liver. Both cellular and humoral immunity may be suppressed during invasion, and immune-related protein synthesis is expected to decrease as protein catabolism is considerably enhanced.

The involvement of various cytokines in metabolic changes in invaded bodies has been revealed in experiments where cytokines themselves are administered, experiments that block the production or action of cytokines, etc. Specifically, the metabolic variations caused by TNF-$\alpha$, IL-1, and IL-6 are: (1) enhanced glycogenolysis, hyperglycemia and hypoglycemia with regard to the glucose metabolism, (for example, Meszaros K et al. "Tumor necrosis factor increases in vivo glucose utilization of macrophage-rich tissues" Biochem. Biophys. Res. Commun., Vol. 149, No. 1: pp. 1-6, 1987 Nov. 30; Tracey, K J et al. "Shock and tissue injury induced by recombinant human cachectin" Science, Vol. 234, No. 4775: pp. 470-474, 1986 October 24; Fukushima, R et al. "Different roles of IL-1 and TNF on hemodynamics and interorgan amino acid metabolism in awake dogs" Am. J. Physiol., Vol. 262, No. 3, Pt. 1: pp. E275-E281, 1992 March), (2) increased muscular decay and amino acid release, increased intestinal glutamine uptake, increased intestinal alanine release, increased hepatic amino acid uptake, and enhanced acute-phase protein synthesis with regard to the amino acid and protein metabolism, (for example, Fukushima, R et al. "Different roles of IL-1 and TNF on hemodynamics and interorgan amino acid metabolism in awake dogs" Am. J. Physiol., Vol. 262, No. 3, Pt. 1: pp. E275-E281, 1992 March; Moldawer, L L et al. "Interleukin 1 and tumor necrosis factor do not regulate protein balance in skeletal muscle" Am. J. Physiol., Vol. 253, No. 6, Pt. 1: pp. C766-C773, 1987 December), and (3) enhanced fatty acid degradation and decreased lipoprotein lipase activity with regard to the lipid metabolism (for example, Feingold, K R et al. "Multiple cytokines stimulate hepatic lipid synthesis in vivo" Endocrinology, Vol. 125, No. 1: pp. 267-274, 1989 July; Grunfeld, C et al. "Tumor necrosis factor: immunologic, antitumor, metabolic, and cardiovascular activities" Adv. Intern. Med., Vol. 35: pp. 45-71, 1990; Feingold, K R et al. "Tumor necrosis factor stimulates hepatic lipid synthesis and secretion" Endocrinology, Vol. 124, No. 5: pp. 2336-2342, 1989 May).

A rational way to prevent the metabolic abnormalities and organ damage caused by cytokines during invasion would be to cause normal cytokine production locally, whilst preventing cytokine spread to the whole body. Such methods include the use of enteral nutrition, $\omega$-3 fatty acids, or growth hormones.

There are several reports regarding differences in cytokine production due to differences in nutrition administration routes during invasive stress. In healthy adults who are not experiencing invasive stress, administration of enteral or intravenous nutrition for one week does not cause any obvious differences in blood TNF-$\alpha$ and IL-6 levels (for example, Lowry, S F et al. "Nutrient modification of inflammatory mediator production" New Horiz., Vol. 2, No. 2: pp. 164-174, 1994 May). However, when administration of enteral or intravenous nutrition continues for seven days and is followed by intravenous injection of endotoxins, systemic reactions, including fever and release of TNF-$\alpha$ and stressor hormones, are reported to be milder for enteral nutrition than for intravenous nutrition (for example, Fong, Y M et al. "Total parenteral nutrition and bowel rest modify the metabolic response to endotoxin in humans" Ann. Surgery., Vol. 210, No. 4: pp. 455-457, 1989 October).

DISCLOSURE OF THE INVENTION

An objective of the present invention is to provide nutritional compositions for use in the nutritional management and therapy of liver failure patients. In addition, another objective of the present invention is to provide nutritional compositions useful for the metabolic and nutritional management of patients under highly invasive stresses such as surgery, infection, and scalds. Furthermore, another objective of the present invention is to provide nutritional compositions useful for the pathological improvement of inflammatory disease patients.

The present inventors discovered that the onset of galactosamine-induced liver damage in rats could be suppressed by nutritional compositions comprising a whey protein hydrolysate, lecithin, a high oleic acid-containing oil, and palatinose as essential ingredients. Furthermore, they discovered that the whey protein hydrolysate suppresses the production of LPS-induced TNF-α and interleukin 6 (IL-6) in vivo. These results showed that the nutritional compositions of the present invention are useful in the nutritional management and therapy of liver disease patients, metabolic and nutritional management of patients under highly invasive stresses such as surgery, infection, or scalds, and pathological improvement of inflammatory diseases.

Figure 1:
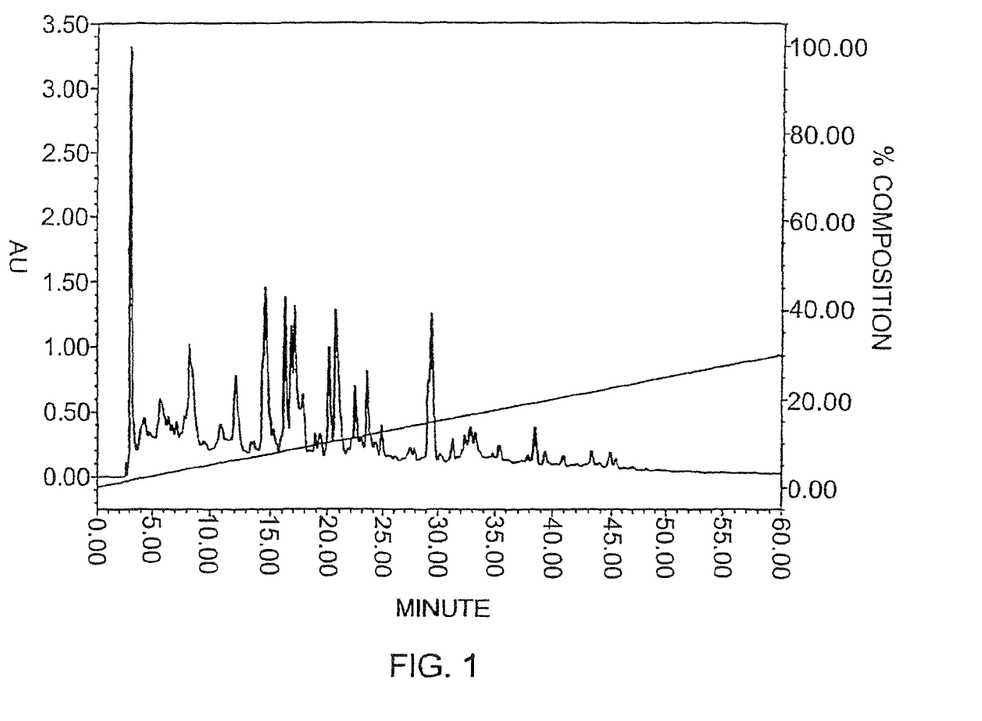
FIG. 1 is a reverse-phase chromatogram of the UF permeate (molecular weight cutoff: 10,000) of a whey protein isolate (WPI) hydrolysate.

Specifically, the present invention comprises:

(1) a nutritional composition for liver disease patients comprising: a milk protein hydrolysate and a protein derived from fermented milk as proteins; a high oleic acid-containing oil and milk lecithin and/or soybean lecithin as lipids; and palatinose as a carbohydrate;

(2) the nutritional composition according to (1), wherein said milk protein is selected from the group consisting of casein, a milk protein concentrate (MPC), a whey protein concentrate (WPC), a whey protein isolate (WPI), α-lactoalbumin, β-lactoglobulin, and lactoferrin;

(3) the nutritional composition according to (1), wherein said fermented milk-derived protein is from a composition in which the whey in fermented milk has been reduced;

(4) the nutritional composition according to (1), wherein said fermented milk-derived protein is from fresh cheese;

(5) the nutritional composition according to (4), wherein said fresh cheese is quark;

(6) the nutritional composition according to (1), wherein said milk protein hydrolysate may be obtained by hydrolyzing a whey protein isolate (WPI) with alkalase from *Bacillus licheniformis*, and trypsin from a porcine pancreas;

(7) the nutritional composition according to (6) which is a permeate obtained by further treatment with an ultrafiltration membrane having a fractionation molecular weight of 10,000;

(8) the nutritional composition according to (7), wherein the chromatogram from reverse phase HPLC separation is shown in FIG. 1;

(9) a nutritional composition for patients under high levels of invasive stress, wherein said nutritional composition comprises: a milk protein hydrolysate and a protein derived from fermented milk as proteins; a high oleic acid-containing oil and milk lecithin and/or soybean lecithin as lipids; and palatinose as a carbohydrate;

(10) the nutritional composition according to (9), wherein said milk protein is selected from the group consisting of casein, a milk protein concentrate (MPC) a whey protein concentrate (WPC), a whey protein isolate (WPI), α-lactoalbumin, β-lactoglobulin, and lactoferrin;

(11) the nutritional composition according to (9), wherein said fermented milk-derived protein is from a composition in which the whey in the fermented milk has been reduced;

(12) the nutritional composition according to (9), wherein said fermented milk-derived protein is from fresh cheese;

(13) the nutritional composition according to (12), wherein said fresh cheese is quark;

(14) the nutritional composition according to (9), wherein said milk protein hydrolysate may be obtained by hydrolyzing a whey protein isolate (WPI) with alkalase derived from *Bacillus licheniformis*, and trypsin from a porcine pancreas;

(15) the nutritional composition according to (14), which is a permeate obtained by further treatment with an ultrafiltration membrane having a fractionation molecular weight of 10,000; and (16) the nutritional composition according to (15), wherein the chromatogram from reverse phase HPLC separation is shown in FIG. 1.

1 Protein 1-1. Milk Protein Hydrolysate

Casein, a whey protein (a whey protein concentrate (WPC), a whey protein isolate (WPI), a α-lactoalbumin (α-La), and β-lactoglobulin (β-Lg)), a milk protein concentrate (MPC or total milk protein (TMP)), and such can be used as protein sources.

Enzymes normally used for hydrolysis of whey proteins are, for example, pepsin, trypsin, and chymotrypsin. However, there are also reports of studies using plant-derived papain, and proteases derived from bacteria and fungi (Food Technol., 48: 68-71, 1994; Trends Food Sci. Technol., 7: 120-125, 1996; Food Proteins and Their Applications: pp. 443-472, 1997). Whey protein-hydrolyzing enzyme activity varies greatly. Pepsin degrades denatured α-La and α-La, but not native β-Lg (Neth. Milk dairy J., 47: 15-22, 1993). Trypsin slowly hydrolyzes α-La but hardly degrades β-Lg (Neth. Milk dairy J., 45: 225-240, 1991). Chymotrypsin rapidly degrades α-La, however slowly degrades β-Lg. Papain hydrolyzes bovine serum albumin (BSA) and β-Lg, but shows resistance to α-La (Int. Dairy Journal 6: 13-31, 1996a). However, under acidic pH, α-La not bound to Ca is completely degraded by papain (J. Dairy Sci., 76: 311-320, 1993).

By controlling the enzymatic degradation of a milk protein and by modifying the protein, the functional characteristics of that protein can be altered over a wide range of pH and processing conditions (Enzyme and Chemical Modification of proteins in Food proteins and their Applications pp. 393-423, 1997 Marcel Dekker, Inc. New York, 1997; Food Technol., 48: 68-71, 1994).

Hydrolysis of peptide bonds increases the member of charged groups and hydrophobicity, decreases molecular weight, and modifies molecular configuration (J. Dairy Sci, 76: 311-320, 1993). Changes in functional properties depend greatly on the degree of hydrolysis. The greatest changes commonly observed in whey protein functionality are increased solubility and decreased viscosity. Often when the degree of hydrolysis is high, hydrolysates will not precipitate, even upon heating, and are highly soluble at pH 3.5 to 4.0. Hydrolysates also have far lower viscosity than intact proteins. This difference is especially prominent when protein concentration is high. Other effects include altered gelation properties, enhanced thermostability, increased emulsifying and foaming abilities, and decreased emulsion and foam stabilities (Int. Dairy journal, 6: 13-31, 1996a; Dairy Chemistry 4, pp. 347-376, 1989; J. Dairy Sci., 79: 782-790, 1996).

Various bioactive oligopeptides derived from milk proteins are known (Yoshikawa, M, "New Horizon in Milk Science", Yoshikawa, M. ed., pp. 188-195, Kougaku Shuppan, 1998; Otani, H., "New Horizon in Milk Science", Yoshikawa, M. ed., pp. 97-99, Kougaku Shuppan, 1998; Otani, H., Milk Science, 47: 183, 1998; Trends in Food Science and Technology, 9: 307-319, 1998). One such example is peptides with angiotensin-converting enzyme (ACE) inhibitor activity (hypertensive effect).

There are reports involving a variety of peptides that may have ACE inhibitory activity, as predicted from measurements in vitro (for example, J. Dairy Res., 67: 53-64, 2000; Br. J. Nutr., 84: S33-S37, 2000). There are research reports on the purification and identification of ACE inhibitory peptides from, hydrolysates using various chromatography techniques (for example, Maruyama, S., & Suzuki, H., Agricultural and Biological Chemistry, 46: 1393-1394, 1982; Miyoshi S. et al., Agri. Biol. Chem., 55: 1313-1318, 1991; Food Science and Biotechnology, 8: 172-178, 1999; Biosci. Biotech. Biochem., 57: 922-925, 1993).

From these reports, ACE inhibitory activity is considered to exist in many fractions obtained using column-based separations. Thus, the molecular characteristics of ACE inhibitory substances are considerably diverse. ACE inhibition is in fact found in various proteins, proteases, and hydrolysates produced under hydrolysis conditions. This fact suggests that a variety of peptides with a range of amino acid sequences may also have ACE inhibitory activity. Due to the chemical diversity of these peptides, hydrolysate purification using chromatography may always be accompanied by a partial loss of active peptides. During hydrolysis, ACE inhibitory activity is continuously created and degraded. When these two processes are optimized, maximum hydrolysate activity results. ACE inhibitory activity is determined by overall hydrolysate peptide compositions, and depends on hydrolase specificity and process conditions.

There is a report on the optimization (using response surface methodology) of whey protein hydrolysis in order to maximize ACE inhibitory activity and keep the required hydrolysis to the minimum (International Dairy Journal 12: 813-820, 2002).

The present invention revealed for the first time that milk protein hydrolysates suppress the in vivo production of LPS-induced TNF-α and IL-6. There have been a number of reports regarding the effect of peptides derived from milk protein on cytokine production. There are reports that peptides derived from bovine casein enhance the production of LPS-induced TNF-α and IL-6 from murine myeloid macrophages (J. Sci. Food Agric., 81: 300-304, 2000). There are also reports that peptides which induce IL-6 production in response to LPS stimulation exist in the supernatant of milk fermented by probiotic Lactobacillus (Milchwissenschaft, 57(2): 66-70, 2002). However, to the best of the present inventors' knowledge, there are no reports on the suppression of inflammatory cytokine production by milk-derived proteins. Also, as in the peptides having the above-mentioned ACE inhibitory activity, peptides which suppress the production of LPS-induced TNF-α and IL-6 may exist in many fractions obtained from various column-based separations.

Therefore, by using as an index the suppressive effect on LPS-induced TNF-α and/or IL-6 production, the conditions for milk protein hydrolysis (denaturation temperature, pH, temperature, hydrolysis time, and enzyme/substrate ratio) can be optimized as per the above-mentioned reference (International Dairy Journal 12: 813-820, 2002). Therefore, the present invention includes the optimized hydrolysis conditions thus obtained.

In addition to the references cited above, many patents (published patent applications and patents) exist with regards to milk protein hydrolysates. Examples include: a patent on the separate hydrolysis of casein and whey protein, followed by adsorption and removal of the hydrophobic portion, and then mixing of the casein and whey proteins in a designated ratio (Japanese Patent No. 2,986,764); a patent on the hydrolysis of whey protein with proteases derived from *Bacillus* and from actinomycetes, followed by the removal of the enzyme and insoluble hydrolysis products (Japanese Patent No. 3,220,638); a patent on a peptide mixture in which the mole ratio of branched-chain amino acids/aromatic amino acids, achieved by enzymatic degradation of β-lactoglubulin, is 10 weight percent or more, where aromatic amino acids are less than 2.8 weight percent, and where the average molecular weight is several hundred to several thousand (Japanese Patent No. 3,183,945); a patent on the selective enzymatic degradation of β-lactoglobulin in whey protein (Japanese Patent No. 2,794,305); and a patent on using proteases derived from *B. licheniformis* and/or *B. subtilis* to hydrolyze whey proteins by the non-pH-stat technique to 15% to 30% (Dextrose Equivalent; DE), and then obtaining the permeate from an ultrafiltration membrane with a cutoff value greater than 10,000 (Japanese Patent No. 3,167,723); and the present invention includes patents and unexamined published patents other than these patents and patent applications.

Whether or not the hydrolysates of the above-mentioned references and patents and patent application scan suppress the production of LPS-induced TNF-α and IL-6 can be investigated using a known assay system (for example, Experimental Medicine Supplementary Vol. "Bio Manual UP Experiment Series", Cytokine Experiment Methods, Miyajima, A., Yamamoto, M. ed., Yodosha, (1997)). Therefore, hydrolysates having the activity to suppress TNF-α and IL-6 production are included in the present invention.

For example, preliminary heating, enzyme substrate ratio (E/S) pH, hydrolyzing temperature, and hydrolyzing time are selected as five parameters for optimization.

Preliminary heating: 65-90° C.
E/S: 0.01-0.2
pH: 2-10
Hydrolyzing temperature: 30-65° C.
Hydrolyzing time: 3 hours to less than 20 hours
Examples of the enzymes used include the following enzymes from Nova Nordisk:

1) Endoproteases
*B. licheniformis*-derived: Alcalase
*B. lentus*-derived: Esperase
*B. subtilis*-derived: Neutrase
Bacteria-derived: Protamex
Porcine pancreas-derived: PTN (trypsin)
2) Exoproteases
*Aspergillus oryzae*-derived: Flavorzyme
Porcine or bovine viscera-derived: carboxypeptidase Examples other than the above-mentioned enzymes include animal-derived pancreatin, pepsin, plant-derived papain, bromeline, endoprotease and exoprotease derived from microorganisms (for example, Lactobacillus, yeasts, molds, and mycobacteria), and their crudely purified material and bacterial homogenates. Furthermore, combinations of *B. licheniformis*-derived Alcalase and porcine pancreas-derived PTN (trypsin) are often used when combining enzymes.

The protein hydrolysates of the present invention include: enzyme hydrolysates which themselves suppress the production of LPS-induced TNF-α and/or IL-6; retained solutions or permeates after ultrafiltration; and commercial milk protein hydrolysates which show similar activity.

Milk protein hydrolysate content is estimated to be 0-9 to 3 g, or preferably 1.2 to 2 g per 100 mL of product. The optimum range can be confirmed by experimentation (for example, by using the inhibition of TNF-α production as an index).

1-2. Fermented Milk-Derived Proteins

Fermented milk (yogurt)-derived proteins have an amino acid score of 100, their ability to be digested and absorbed is elevated by fermentation, and they have a high nutritional value. Ingredients include those in which the aqueous portion (whey) in fermented milk (yogurt) has been reduced (for example, Japanese Patent No. 3,179,555).

While there are many kinds of fresh cheeses, including cottage, quart, string, neuchatel, cream cheese, mozzarella, ricotta, and mascarpone, quark is the appropriate source. The procedure for producing quark is well known (for example, Unexamined Published Japanese Patent Application No. (JP-A) Hei6-228013).

The content of fermented milk-derived proteins may be 2-6 g, or preferably 2.5-4.5 g of protein per 100 mL of product.

2. Lipids
2-1. Phospholipids

As phospholipids, a combination of milk-derived lecithin and soybean-derived lecithin or egg yolk lecithin is used. Milk-derived lecithin alone may also be used. In fields such as biochemistry, medicine and pharmacology, the term "lecithin" is used only for phosphatidylcholine. However in commercial or industrial fields, lecithin is used as a general term for phosphatidylcholine, phosphatidylethanolamine, phosphatidylinositol, phosphatidic acid, and a mixture of other phospholipids. In "Japan's Specifications and Standards for Food Additives", 7th edition (1999), lecithin is defined as "a substance obtained from oilseed or animal sources, whose main component is phospholipids". In the present invention, milk-derived phospholipids are also collectively referred to as "milk-derived lecithin".

Milk-Derived Lecithin

Milk phospholipid (milk lecithin) comprises sphingomyelin (SM), phosphatidyicholine (PC), phosphatidylethanolamine (PE), phosphatidylinositol (PI), phosphatidylserine (PS), and lysophosphatidylcholine (LPC), and only exists in milk fat globule membranes (MFGM). The composition of the MFGM phospholipid fraction is shown in Table 1 (Bulletin of Japan Dairy technical Association, Vol. 50: pp. 58-91, 2000).

As indicated in Table 1, milk lecithin characteristically includes a large amount of SM, which is not contained in soybean lecithin. When administered to rats, milk lecithin increases DHA content in the brain and liver to a greater extent than does soybean lecithin. Also, when compared to soybean or egg yolk lecithin, milk lecithin is more effective at improving hyperlipidemia and fatty liver. Furthermore, SM is known to be involved with the cholesterol metabolism, for example, SM regulates HMG-CoA reductase activity involved in the biosynthesis of cholesterol, and is involved in the regulation of cholesterol absorption in the intestinal tract. Accordingly, it is thought that PC and PE's ability to improve lipid metabolism may be further enhanced by SM (Sasaki, HE. Milk Science 51(2): 93-94, 2002).

TABLE 1

| Phospholipid component | Weight % |
| --- | --- |
| Sphingomyelin | 22 |
| Shosphatidylcholine | 36 |
| Phosphatidylethanolamine | 27 |
| Phosphatidylinositol | 11 |
| Phosphatidylserine | 4 |
| Lysophosphatidylcholine | 2 |

Examples of substances having a large content of MFGM include freeze-dried WPI byproducts produced by combining ultrafiltration (UF) and microfiltration (MF) (MF retained solution), fractions in which anhydrous milk fat (AMF) is removed from cream or butter (butter serum), and fractions in which AMF is removed from whey cream (whey cream serum). Methods for obtaining phospholipid concentrates using these as raw materials are well known (for example, JP-A Hei7-173182 is included in the present invention).

Soybean Lecithin

While soybean lecithin is widely used as a natural food additive in the field of foods and food products, polyenephosphatidylcholine is also used as a drug (applications: for the improvement of liver function, fatty liver, and hyperlipidemia in chronic liver disease). Examples of the physiological functions of soybean lecithin include the regulation of the morphology and function of biomembranes, the improvement of: lung functions; arteriosclerosis; lipid metabolism; and liver lipid metabolism, and the improvement and advancement of nerve function (Food Processing and Ingredients, Vol. 29(3): 18-21, 1994).

"Natural" lecithin products are normally ranked according to their PC content. Various types of lecithins upgraded according to their use have been produced. As Table 2 indicates, soybean lecithin products are conveniently categorized according to differences in the main ingredient PC, based on purification and soybean lecithin fractionation (Fujikawa, T., Oil Chemistry, Vol. 40(10): 951-958, 1991).

TABLE 2

| Type | PC content (%) |
| --- | --- |
| Paste lecithin | 15-20 |
| Purified lecithin | 20-25 |
| Extracted lecithin | 30-40 |
| PC concentrated lecithin | 45-60 |
| PC highly purified lecithin | 75-95 |
| Phospholipids (PC, PE, PS, PG, etc.) | individually 98% or more |

Milk lecithin and soybean lecithin may be used alone or in combination. The total content per 100 mL of product may be 0.1-0.5 g, or preferably 0.2-0.3 g. Oleic acid content may be 2-3 g, or preferably 2.1-2.5 g.

2-2. Other Lipids

The Ministry of Health, Labour and Welfare recommends that the preferred intake ratio of saturated fatty acids (SFA: palmitic acid, stearic acid, etc.): monovalent unsaturated fatty acids (MUFA: oleic acid, etc.): polyvalent unsaturated fatty acids (PUFA: linolic acid, linolenic acid, etc.) be changed From the former 1:1.5:1 to 3:4:3, and that the n-6 fatty acid: n-3 fatty acid ratio be made 4:1. One of the reasons for this recommendation is that in Japan it is difficult to practice a diet in which the intake ratio of MUFA is 1.5 times that of SFA and PUFA. Therefore, in the fatty acid composition of lipids, MUFA content is improved. Oleic acid, which is a monovalent unsaturated fatty acid, is mixed into the fatty acid composition to compose more than 30%, or preferably 30-60% of the mixture. Lipid sources containing a large amount of oleic acid include high oleic acid-containing sunflower oil, rapeseed oil, olive oil, high oleic acid safflower oil, soybean oil, corn oil, and palm oil. Furthermore, nutritionally adjusted oils and fats (NOF Corporation) are also a lipid source containing oleic acid. Sunflower oil, rapeseed oil, olive oil, and a mixture containing olive oil may be used. An appropriate oleic acid content for each 100 g of product is selected from 1-6 g. Furthermore, polyvalent unsaturated fatty acids such as DHA, EPA, and arachidonic acid, and medium-chain fatty acids such as caprylic acid, capric acid, and lauric acid are added to adjust the SFA:MUFA:PUFA ratio to 3:4:3.

3. Carbohydrates and Dietary Fiber

The main carbohydrate as referred to in the present invention is Palatinose. Examples of other carbohydrates include sugar alcohols (sorbitol, xylitol, maltitol, etc.), honey, granulated sugar, glucose, fructose, and invert sugar.

Palatinose includes palatinose syrup, reduced palatinose, or palatinose starch syrup. Palatinose starch syrup is a liquid substance in the form of starch syrup containing as the main ingredient an oligosaccharide such as tetrasaccharide, hexasaccharide, and octasaccharide produced when palatinose is polymerized by dehydration. In a manner similar to sucrose, palatinose is digested into glucose and fructose and then absorbed (Goda, T. et al., Journal of Japanese Society of Nutrition and Food Science, Vol. 36(3): 169-173, 1983). However, since palatinose hydrolysis is slow, at ⅕ that of sucrose (Tsuji, Y. et al., J. Nutr. Sci. Vitaminol., 32: 93-100, 1986), blood glucose and insulin concentration after ingestion are maintained at a constant level for a long time (Kawai, K. et al., Endocrinol, Japan, 32(6): 933-936, 1985).

Palatinose content per 100 mL of product may be 4-15 g, or preferably 5-6 g.

The energy ratio for proteins, lipids, and carbohydrates is nearly the same as that in the "Sixth Revised Nutritional Requirements of the Japanese", and is considered to be 15-25 kcal for proteins, 20-30 kcal for lipids, and 45-65 kcal for carbohydrates.

Dietary fiber can be divided into water-soluble dietary fiber and insoluble dietary fiber. Indigestible oligosaccharides, lactulose, lactitol, or raffinose can be used as water-soluble dietary fiber. Indigestible oligosaccharides function to improve the intestinal environment by reaching the large intestine undigested and contributing to the activation and growth of intestinal bifidobacteria. Lactulose is a synthetic disaccharide consisting of galactose and fructose, and is used as a basic pharmaceutical agent for hyperammonemia (Bircher, J. et al., Lancet: 890, 1965). Chronic recurrent hepatic encephalopathy due to chronic hepatic failure responds well to lactulose administration, to the infusion of special amino acids for hepatic failure (Fischer solution), and such. Lactitol (β-galactosyl-sorbitol), which should be considered a second generation lactulose, has similar clinical effects as lactulose, (Lanthier, P L. and Morgan, M., Gut, 26: 415, 1985; Uribe, M., et al., Dig. Dis. Sci., 32: 1345, 1987; Heredia, D. et al., J. Hepatol, 7: 106, 1988; Riggio, O., et al., Dig. Dis. Sci., 34: 823, 1989), and is currently used as a therapeutic agent for hyperammonemia.

Other candidates for water-soluble dietary fibers include products that improve lipid metabolism (decreasing cholesterol and triglycerides) such as pectin (protopectin, pectinic acid, pectic acid), products of guar gum enzyme degradation, and tamarind seed gum. The products of guar gum degradation suppress the elevation of blood glucose levels, cutting back on insulin (Yamatoya, K. et al. journal of Japanese Society of Nutrition and Food Science, Vol. 46: 199, 1993). Furthermore, candidates for water-soluble dietary fiber include, as high molecular weight water-soluble dietary fiber: konjac glucomannan, alginic acid, low molecular weight alginic acid, psyllium, gum arabic, seaweed polysaccharides (cellulose, lignin-like substances, agar, carrageenan, alginic acid, fucodine, and laminarin), gums produced by microorganisms (welan gum, curdlan, xanthan gum, gellan gum, dextran, pullulan, and rhamsan gum), other gums (seed-derived locust bean gum, tamarind gum, tara gum, sap-derived karaya gum, and tragacanth gum); and as low molecular weight water-soluble dietary fiber: polydextrose, indigestible dextrin, maltitol and such.

Insoluble dietary fiber increases the bulk of undigested material in the large intestine and shortens its passage time. This increases the frequency of defecation and the quantity of stool. Examples of candidates for insoluble dietary fiber include cellulose, hemicellulose, lignin, chitin, chitosan, soybean dietary fiber, wheat bran, pine fiber, corn fiber, and beet fiber.

4. Vitamins

There are currently 13 kinds of known vitamins. Of these, vitamins A, K and the B complex ($B_1$, $B_2$, nicotinic acid, $B_6$, pantothenic acid, folic acid, $B_{12}$, and biotin), are known to be deeply involved with the liver. The main concerns in relation to hepatopathy, are deficiency and overabundance of vitamin A, deficiency of the vitamin B complex, and overabundance of vitamin K.

When obstructive jaundice or the like causes a shortage of bile in the intestinal tract, vitamin A absorption rate decreases, resulting in vitamin A deficiency. Furthermore, under conditions of low protein nutrition, retinol binding protein (RBP) production decreases. Thus, vitamin A is not delivered to target organs, and symptoms of deficiency are expressed. In cases of decompensated cirrhosis, symptoms of poisoning will appear by a relatively small excess of vitamin A. In chronic liver disease, dysfunctional utilization of vitamin B complex is observed. Since vitamin K synthesized by enterobacteria can also be utilized, a deficiency of vitamin K is not usually seen. However, when there is a shortage of bile in the intestinal tract due to obstructive jaundice, a decrease in the vitamin K absorption rate can occur.

Therefore, the present nutritional compositions can contain an appropriate amount of each vitamin based on the vitamin's relationship with the liver.

5. Minerals

The electrolytes normally in question in humoral regulation are sodium, chlorine, potassium, phosphorus, calcium, and magnesium. When preparing a prescription of minerals, three factors are considered: (1) whether the minerals to be taken up into cells are sufficiently supplied, (2) whether the patient's endocrinal environment can sufficiently cope with the quantity and variety of nutritional substrates to be administered, and (3) whether the volume of water administered is adequate for measuring the osmotic load on the kidney, and for maintaining an appropriate urine osmotic pressure.

Iron and naturally-derived trace elements such as mineral yeasts such as copper, zinc, selenium, manganese, and chromium yeasts can also be included. Copper gluconate, zinc gluconate and such may also be used.

The nutritional compositions have an osmotic pressure of approximately 300-1000 mOsm/L, and for example, can have an osmotic pressure of approximately 300-750 mOsm/L. When measured at room temperature, the nutritional compositions have a viscosity of approximately 5-40 cp (1 cp=0.001 Pa?s), or preferably less than 20.

The caloric content of the nutritional compositions is approximately 1-2 kcal/ml, or preferably 1-1.5 kcal/ml.

The nutritional compositions are preferably in a directly usable form. In this form, the compositions can be administered via a tube from the nose through to the stomach and jejunum (a portion of the small intestine), or ingested orally. Such nutritional compositions may take various forms, for example, fruit juice- or milkshake-type beverages. The nutritional compositions may also be a soluble powder that can be reconstituted before use.

The nutritional compositions may include various flavors (for example, vanilla), sweeteners, and other additives. Artificial sweeteners such as aspartame can be used.

Furthermore, 5 mg to 500 mg (0.005% to 0.5%) of champignon extract can be added to reduce fecal odor, and 10 μg to 200 μg (0.00001% to 0.0002%) of carotenoid preparation (for example, α-carotene, β-carotene, licopine, and lutein) can be added for nutritional fortification.

Furthermore, catechin, polyphenols, and such can also be included as antioxidants.

Nutritional compositions can be prepared, for example, by mixing proteins, carbohydrates, and lipids in the combinations shown in Table 3. In this case, emulsifiers can be placed in the mixture.

Preparation of the nutritional compositions of this invention can be carried out by methods well known in the art. These methods include, for example, advance heat-sterilization of a liquid nutritional composition followed by filling it aseptically into a container (for example, a method that uses both UHT sterilization and aseptic packaging), or pouring a liquid nutritional composition into a container, and then heat-sterilizing the container (for example, using an autoclave).

When the present invention is used as a liquid, homogenizing substances can be poured into a can-like container, and then retort sterilized, or alternatively heat-sterilized again at approximately 140-145° C. for approximately 5-8 seconds, cooled, then aseptically filled. When used as a powder, homogenizing substances may, for example, be spray dried.

The nutritional compositions of this invention can be used as food for the nutritional management of acute hepatitis (fulminant hepatitis), chronic hepatitis, compensated cirrhosis, and decompensated cirrhosis. The nutritional compositions of this invention are especially useful for nutritional management of chronic hepatic failure with the possibility of developing hepatic encephalopathy. In particular, the nutritional compositions of this invention can be used as nutritional supplements for patients with chronic hepatic failure who are capable of food intake.

Furthermore, the nutritional compositions of this invention can be used for the nutritional management of patients under invasive stress such as surgery, infection, and scalds.

The nutritional compositions of this invention can also be used as food in therapeutic diets for liver disease patients (diets for liver disease), or as tubal or enteral nutritional compositions.

The administration of nutritional compositions differs depend-ng on the condition, weight, and age of the patient, and whether the nutritional composition is the only source of nutrition. The physician in charge determines the amount to be administered.

BEST MODE FOR CARRYING OUT THE INVENTION

The present invention will be explained in detail below with reference to Examples and Test Examples, but it is not to be construed as being limited thereto.

Example 1

Preparation of a Whey Protein Hydrolysate

A whey protein isolate (WPI, Davisco) containing approximately 90% dry proteins was dissolved in distilled water to form an 8% (w/v) protein solution. The proteins were denatured by heat treatment of the solution at 85° C. for two minutes. The pH of the solution after this heat treatment was approximately 7.5. Hydrolysis was performed by adding Alcalase 2.4 L (enzyme, Novozymes) at a concentration of 2.0 relative to the substrate, and this mixture was reacted for three hours at 55° C. PTN 6.0S (Novozymes Japan), which is pig-derived trypsin, was then added at a concentration of 3.0% relative to the substrate, and this mixture was reacted for three hours at 55° C. Complete hydrolysis took six hours. The pH at reaction completion was approximately 7.0. The whey protein hydrolysate was centrifuged (20,000×g, 10 min), then treated with a UF membrane with a fractionation molecular weight of 10,000 (Millipore, Ultrafree-MC).

The permeate was subjected to reverse-phase HPLC (chromatogram shown in FIG. 1).

Conditions
Sample: UF permeate of the whey protein hydrolysate
Column: C18 SG120 (Shiseido) 4.6 mmφ×250 mm
Eluate: A; 0.1% trifluoroacetic acid aqueous solution/acetonitrile 5/95
  B; 0.1% trifluoroacetic acid aqueous solution/acetonitrile 32/68
  A-->B 60-minute linear concentration gradient
Flow rate: 1 mL/min
Detection: 215 nm (UV/visible detector)

Example 2

Preparation of Nutritional Compositions

Nutritional compositions containing the ingredients shown in Table 3 were prepared using standard methods. The whey protein hydrolysate prepared in Example 1 was used. Platinose can be obtained from Shin Mitsui Sugar Co., and freshly prepared oil and fat from NOF Corporation. Milk-derived phospholipid can be obtained by following, for example, the method described in JP-A Hei7-173182. An example is shown below:

After adding 2000 mL of 99.5% ethanol to 800 g of butter serum (BAEF) (Corman), the mixture was stirred for five hours, then suction filtered. The filtrate was concentrated under reduced pressure to yield 160 g of crude lipid. 480 mL of acetone was added to this crude lipid, and the mixture was stirred for 0.5 hours and then suction filtered. 480 mL of acetone was added to the residue, and the mixture was stirred for 0.5 hours, suction filtered, and the residue dried in vacuo to yield 50 g of phospholipid concentrate.

TABLE 3

| Ingredients | | Sources | Ingredient composition per 100 mL |
|---|---|---|---|
| General ingredients | Protein | Whey protein hydrolysate | 1.21 g |
| | | Fermented milk-derived protein | 2.93 g |
| | Lipid | Prepared oils and fats | 3.03 g |
| | | Milk-derived phopholipid | 0.09 g |
| | | Soybean lecithin | 0.15 g |
| | Carbohydrate | Palatinose | 5.59 g |
| | | Dextrin | 6.20 g |
| | | Maltodextrin | 1.52 g |
| | Fiber | Indigestive dextrin | 1.00 g |
| | | Pectin | 0.42 g |
| | | Citric acid Champignon extract Sodium bicarbonate | 260 mg |
| Vitamins | | Vitamin A | 208 IU |
| | | Vitamin D | 22 IU |
| | | Vitamin E | 3.14 mg |
| | | Vitamin $B_1$ | 0.15 mg |
| | | Vitamin $B_6$ | 0.38 mg |
| | | Niacin | 2.3 mg |
| | | Pantothenic acid | 0.63 mg |
| | | Vitamin $B_2$ | 0.21 mg |
| | | Vitamin $B_{12}$ | 0.63 µg |
| | | Carotene | 0.015 mg |
| | | Folic acid | 52 µg |
| | | Vitamin C | 52 mg |
| Minerals | | Potassium | 128 mg |
| | | Sodium | 77 mg |
| | | Calcium | 63 mg |
| | | Magnesium | 22 mg |
| | | Iron | 1 mg |
| | | Zinc | 1 mg |
| | | Copper | 0.30 mg |
| pH | | | 3-4 |
| Osmotic pressure (mOsm/L) | | | Approximately 637 |

Prepared oils and fats include 93% high oleic sunflower oil and 7% perilla oil, and n-6/n-3 is 1.54. This composition is shown in Table 4.

TABLE 4

| Fatty acids | % Content |
|---|---|
| Saturated fatty acid | 7.6 |
| Oleic acid | 80.0 |
| Linoleic acid | 6.4 |
| Linolenic acid | 4.2 |

The composition of milk-derived phospholipids is shown in Table 5.

TABLE 5

| Phospholipids | % |
|---|---|
| Phosphatidylcholine | 24.2 |
| Phosphatidylethanolamine | 20.4 |
| Sphingomyelin | 17.1 |

Test Example 1a

Galactosamine Hepatopathy Suppressive Effect (1)

The ability of the nutritional composition of the present invention, and of Meibalance C as a comparative control, to suppress rat galactosamine hepatitis was investigated. Meibalance C [Meiji Dairies Corp.] is an integrated nutritious liquid food product in a semi-digested form.

?Materials and Methods

Male Sprague-Dawley strain rats (six weeks old, Japan SLC) were reared for a preliminary one week and then divided according to weight into two groups: that raised with the nutritional composition shown in Table 3 (n=8); and that raised with Meibalance C (n=8).

D-galactosamine?HCl (Wako Pure Chemicals) was dissolved in physiological saline to 200 mg/mL, and administered intraperitoneally to the rats in each group at a dose of 300 mg/kr. This day was taken as day zero. After administration, the rats' feed was switched either to the nutritional composition or to Meibalance C. On day seven, galactosamine hydrochloride was administered intraperitoneally to the rats in each group at a dose of 600 mg/kg. On day nine, after a four-hour fast and under diethyl ether anesthesia, blood was collected from the abdominal aorta. Serum was obtained by centrifugation (3,000 rpm, ten minutes), and then stored at −20° C. until measured (the following day). Ammonia concentration in the serum was measured on the day of blood collection. Furthermore, the liver and pancreas were removed and their weights were measured. Biochemical tests on AST (GOT), ALT (GPT), total protein, albumin, ammonia, cholesterol, and triglyceride in the serum were performed using Fuji Dry Chem. Hepatic weight and pancreatic weight were measured, and autopsies were performed. During the experiment, the animals could freely access feed and water. Body weight and feed intake were measured.

Biochemical test results are shown as the average value±standard deviation. For statistical treatment, Student's t Tests were used for even distribution, and Mann-Whitney tests were used for uneven distribution. Significance level was set at less than 5%.

Figure 2:
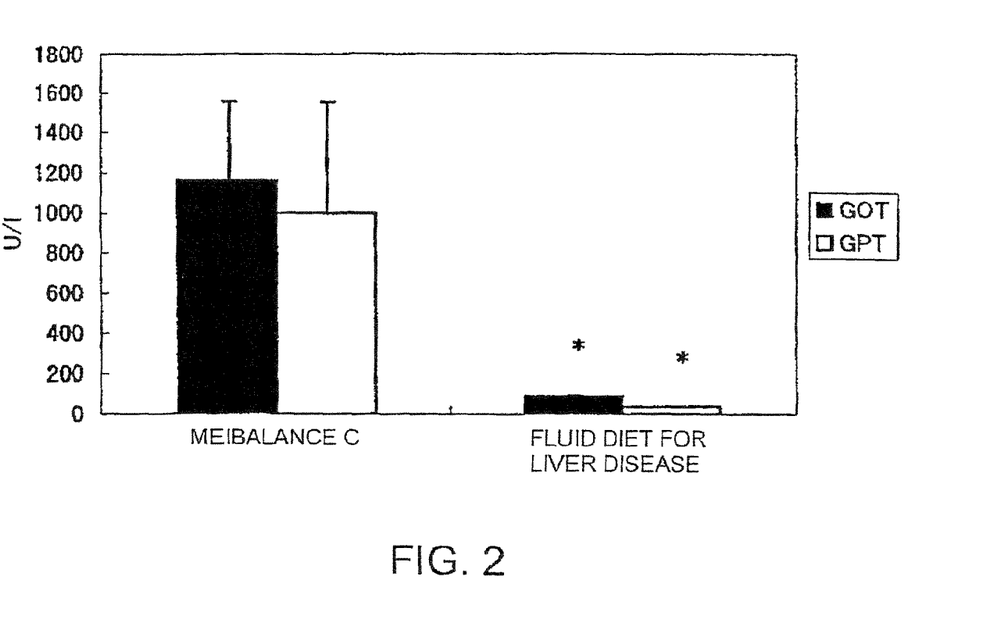
FIG. 2 shows the effect of the nutritional composition and Meibalance C on the suppression of GOT and GPT elevation in galactosamine hepatopathy model rats.

FIG. 2 shows the results of GOT and GPT measurements. Table 6 summarizes the results of measurements on body weight, feed intake, hepatic weight, pancreatic weight, total protein, albumins ammonia, cholesterol, and triglyceride level.

TABLE 6

| Data Item | Meibalance C | Nutritional composition |
|---|---|---|
| Body weight (g) | 249.4 ± 2.8 | 274.0 ± 3.0* |
| Amount of feed intake (g) | 169.7 ± 1.8 | 168.5 ± 6.9 |
| Hepatic weight/body weight × 100% | 2.99 ± 0.12 | 4.13 ± 0.09* |
| Pancreatic weight/body weight × 100% | 0.27 ± 0.01 | 0.22 ± 0.01* |
| <<Biochemical Tests>> | | |
| Total protein (g/dl) | 4.6 ± 0.2 | 5.8 ± 0.1* |
| Albumin (g/dl) | 3.1 ± 0.2 | 3.7 ± 0.1* |
| Ammonia (µg/dl) | 314.9 ± 27.4 | 177.0 ± 21.2* |
| Cholesterol (mg/dl) | 32.9 ± 2.4 | 63.8 ± 2.6* |
| Triglyceride (mg/dl) | 106.0 ± 11.4 | 79.4 ± 8.2* |

*p < 0.05

As shown in FIG. 2, in galactosamine hepatopathy models, serum GOT and GPT levels increased in the group taking Meibalance C, while they were significantly suppressed in the group taking the nutritional composition. Furthermore, total protein, albumin, cholesterol and triglyceride levels in the sera of the nutritional composition group were significantly increased relative to the Meibalance C group, whilst the ammonia level was significantly (p<0.05) suppressed.

Although feed intake in the two groups was almost the same, body weight, hepatic weight, and pancreatic weight of the nutritional composition group was significantly (p<0.05) increased compared to the Meibalance C group.

Measuring GOT and GPT activity in the serum mainly allows the degree of organic disorder to be understood, since GOT and GPT escape into the blood when degeneration or necrosis of hepatocytes occurs. Although total serum protein, albumin, cholesterol and triglyceride levels do not necessarily indicate changes that parallel organic disorders, they are useful in evaluating effects on liver function, including preliminary abilities such as protein synthesis and lipid metabolism.

According to these results, the nutritional compositions of this invention are expected to be effective for nutritional treatment of chronic hepatic failure.

Test Example 1b

Galactosamine Hepatopathy Suppressive Effect (2)

Six-week old Balb/c mice (Japan SLC) were reared for a preliminary one week using AIN-93M (Oriental Yeast), and then divided according to weight into groups of eight mice. The mice were then raised for eight days using Hepas (Morinaga Clinico) and a nutritional composition mixed according to the composition of Table 7 that was retort sterilized after filling into a can-like container and freeze dried. On the eighth day of rearing, D-galactosamine (Wako Pure Chemicals) dissolved in PBS was administered to each mouse at a dose of 400 mg per kg body weight. LPS (Wako Pure Chemicals) was then administered intraperitoneally at a dose of 10 μg per kg body weight. Blood was collected from the tail vein eight hours after administration. On the following day and under ether anesthesia, blood was collected from the artery. The animals could freely access feed and water. The blood was centrifuged to separate the serum, and GOT and GPT were measured by Fuji Dry Chem. The results are indicated as average values±standard deviations, and significant difference tests were performed using Mann-Whitney tests (*: p<0.05).

TABLE 7

Composition of fluid diet for liver disease

| Sources | Ingredients | Content per 100 mL | Units |
|---|---|---|---|
| Whey protein hydrolysate | Whey peptide | 1.83 | g |
| NFL quark | Quark | 3.74 | g |
| Palatinose | Palatinose | 6.15 | g |
| NSD700 | Maltodextrin | 6.40 | g |
| Pine Fibre C | Indigestive dextrin | 0.73 | g |
| Thickener | Pectin | 0.80 | g |
| New prepared oil and fat | Oleic acid | 2.597 | g |
| Lecithin F (soybean oil) | Phospholipid | 0.133 | g |
| Vitamin A-50 oil | Vitamin A | 0.11 | mg |
| Vitamin AD oil | Vitamin D | 0.561 | mg |
| Natural vitamin E | Vitamin E | 6.26 | mg |
| Thamine hydrochloride | Vitamin B1 | 0.292 | mg |
| Pyridoxine hydrochloride (V. B6) | Vitamin B6 | 0.459 | mg |
| Nicotinic acid amide (niacin) | Niacin | 2.42 | mg |
| Calcium pantothenate | | 0.854 | mg |
| Riboflavin (V. B2) | Vitamin B2 | 0.235 | mg |
| Cyanocobalamin (V. B12) | Vitamin B12 | 1.14 | μg |
| Water-soluble multicarotenoid | Carotene | 0.426 | mg |
| Folic acid | | 75 | μg |
| Sodium L-Ascorbate (V. Can) | Vitamin C | 80.8 | mg |
| Potsssium phosphate | Potassium | 0.145 | g |
| Sodium chloride | Sodium | 0.1126 | g |

TABLE 7-continued

Composition of fluid diet for liver disease

| Sources | Ingredients | Content per 100 mL | Units |
|---|---|---|---|
| Calcium lactate | Calcium | 0.5824 | g |
| Magnesium chloride | Magnesium | 0.0426 | g |
| Citric acid | | 0.35 | g |
| Ferrous sulfate | Iron | 0.00454 | g |
| Sodium hydrogen carbonate | | 0.1125 | g |

Figure 3:
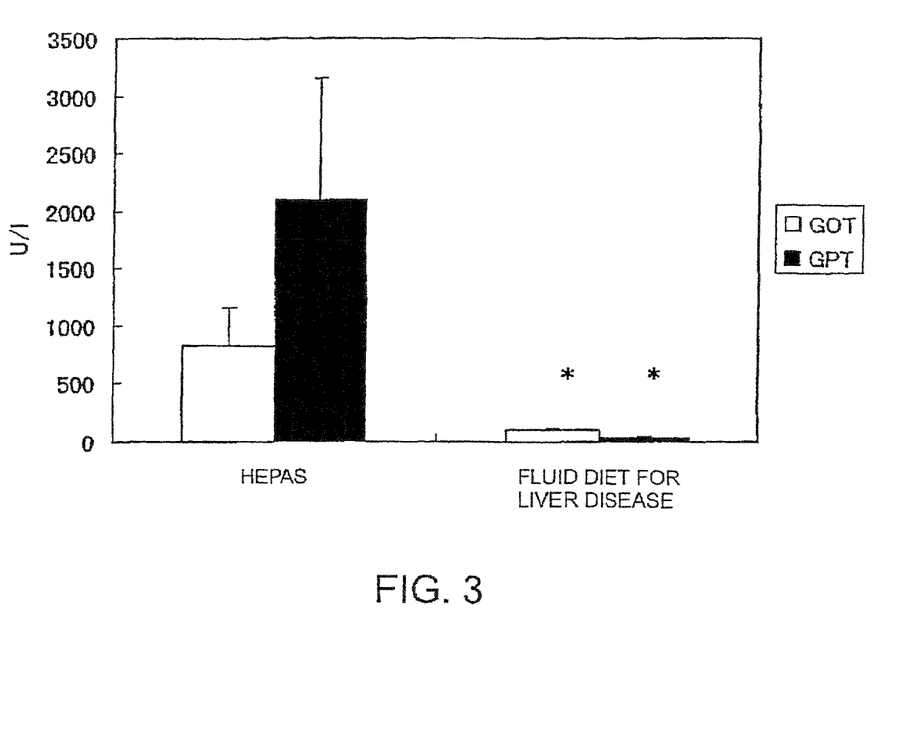
FIG. 3 shows the change in blood GOT and GPT concentrations after galactosamine administration.

Currently, Hepas is the only fluid diet for liver disease available on the market. The effects of Hepas were compared with the effects of the fluid diet for liver disease prepared according to the composition in Table 7. Galactosamine and LPS were intraperitoneally administered to mice, and GOT and GPT levels were investigated eight and 24 hours later. As FIG. 3 shows, Hepas resulted in increased GOT and GPT, and induction of hepatitis. On the other hand, when compared to Hepas, the fluid diet for liver disease of the present invention resulted in significant suppression of GOT and GPI increases.

In the above-mentioned results, Hepas was not observed to have an effect in suppressing hepatitis. On the other hand, the present invention's fluid diet for liver disease was confirmed to be effective in suppressing hepatitis in the galactosamine/LPS-induced mouse hepatitis model.

Test Example 1c

Viral and Autoimmune Hepatopathy Suppressive Effect

Six-week old Balb/c mice (Japan SLC) were reared for a preliminary one week using AIN-93M (Oriental Yeast), and then divided according to weight into groups of ten mice. Their feed was then changed to WPI (Davisco) or experimental feeds in which the casein in AIN-93M (containing 14% casein) was replaced with the whey protein hydrolysate prepared in Example 1, such that the whey protein hydrolysate content would amount to 25% and 50% of the feed protein content. The mice were then raised for 14 days. On the 14th day, ConA (Sigma) dissolved in PBS was injected intravenously at a dose of 15 mg per kg body weight. Blood was collected from the tail vein 2, 4, and 8 hours after administration. On the following day and under ether anesthesia, blood was collected from the artery. The animals could freely access feed and water. The blood was centrifuged to separate the serum, and GOT and GPT were measured by Fuji Dry Chem. TNF-α cytokine levels were measured using ELISA (Amersham Bioscience). Results are indicated as average values±standard deviations, and significant difference tests were performed using Mann-Whitney's U-tests (*: p<0.05).

Figure 4:
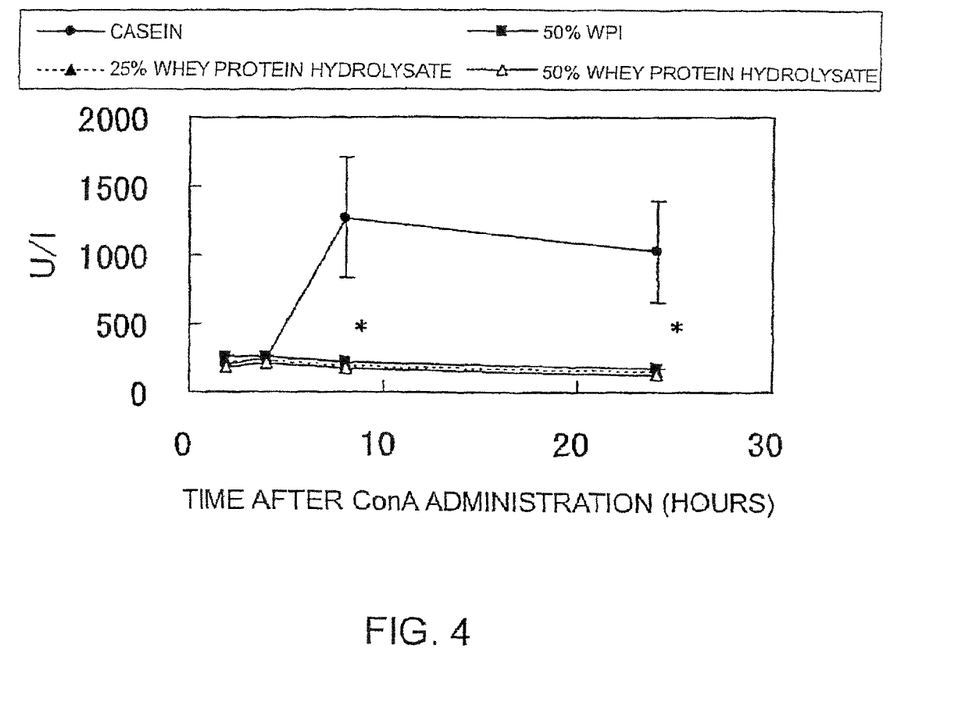
FIG. 4 shows the change in blood GOT concentration after ConA administration.
Figure 5:
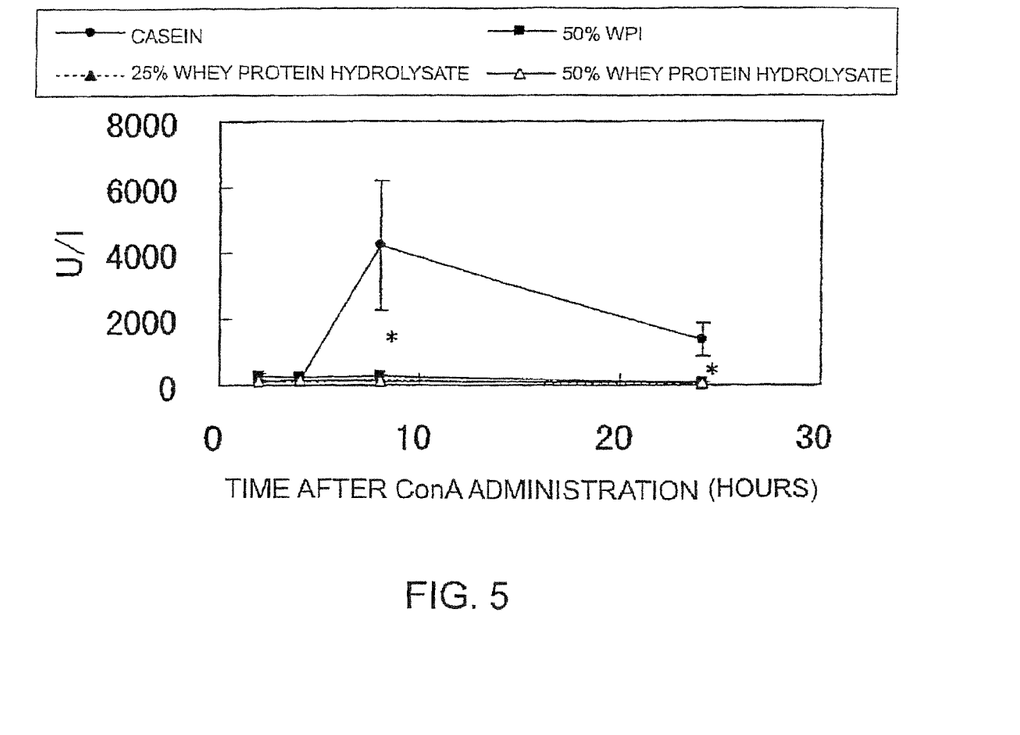
FIG. 5 shows the change in blood OPT concentration after ConA administration.
Figure 6:
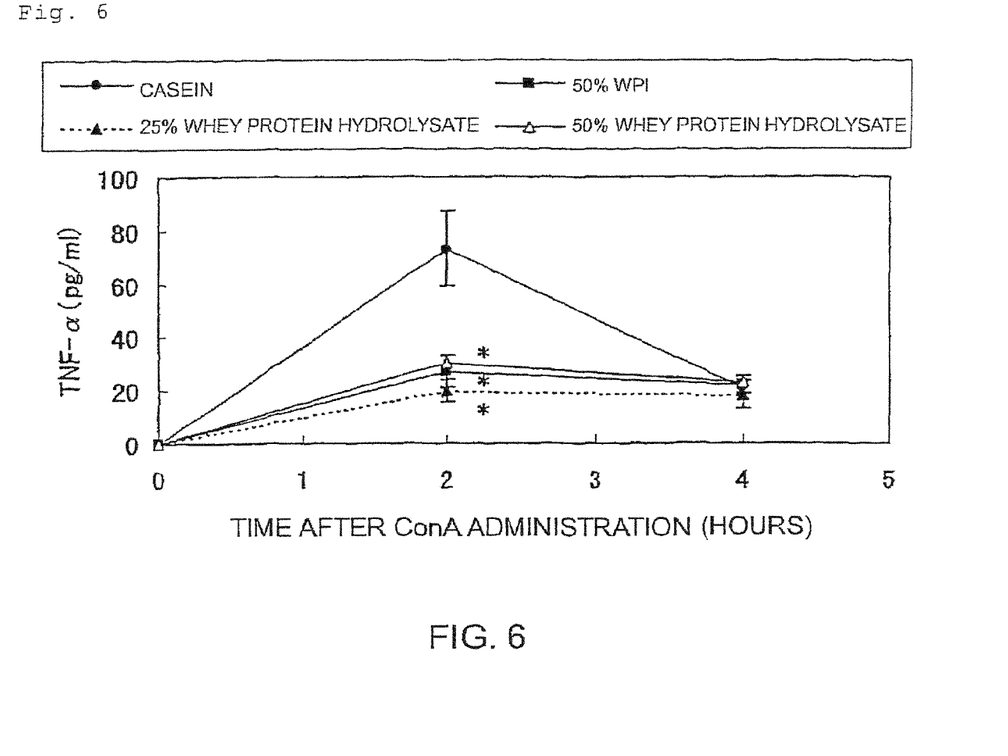
FIG. 6 shows the change in blood TNF-α concentration after ConA administration.

In the casein group, GOT and GPT, which are indices of hepatitis, increased eight to 24 hours after ConA administration. On the other hand, in the WPI and whey protein hydrolysate groups, GOT and GPT increases were significantly suppressed (FIGS. 4 and 5). The 25% whey protein hydrolysate group was confirmed to show effects equal to or stronger than those observed in the 50% WPI group. Therefore, WPI-derived whey protein hydrolysate is expected to have a greater effect than WPI. Cytokine production in these same individuals was also investigated at the same time. In the casein group, serum TNF-α concentration increased two hours after ConA administration, and decreased four hours after (FIG. 6). Two hours after ConA administration, TNF-α concentration in the WPI group and whey protein hydrolysate groups was significantly lower than in the casein group. WPI and whey protein hydrolysate were confirmed to be effective in suppressing TNF-α secretion. Suppression of cytokine production may also suppress hepatitis, induction, and thus may also suppress increases of GOT and GPT. As described above, in the ConA-induced hepatopathy model, WPI-derived whey protein hydrolysate was confirmed to suppress hepatopathy.

Test Example 2

Anti-Inflammatory Effect of the Whey Protein Hydrolysate

<Method>

Six-week old male ICR strain mice (Japan SLC) were reared for a preliminary one week and then divided into three groups of six mice, such that the average body weight for each group was equal. As a protein source, experimental feed was prepared from purified feed (AIN-93M) by adding 14% by weight of 10% casein (control group), 50% casein+50% WPI (Davisco Foods), or 50% casein+50% whey protein hydrolysate (as prepared in Example 1). The mice were then raised for seven days.

After breeding, lipopolysaccharide (LPS) was interperitoneally administered to the rats at a dose of 1.4 μg/g body weight. Blood was collected from the eye socket 90 minutes later, and serum was obtained by centrifugation (10,000×g, 15 minutes). Serum TNF-α and IL-6 were measured using an ELISA kit (Amersham bioscience). Significant difference tests among the groups were performed using Fisher's PLSD. Serum TNF-α concentration and IL-6 concentration are shown in FIGS. 7 and 8 respectively.

<Results>

Figure 7:
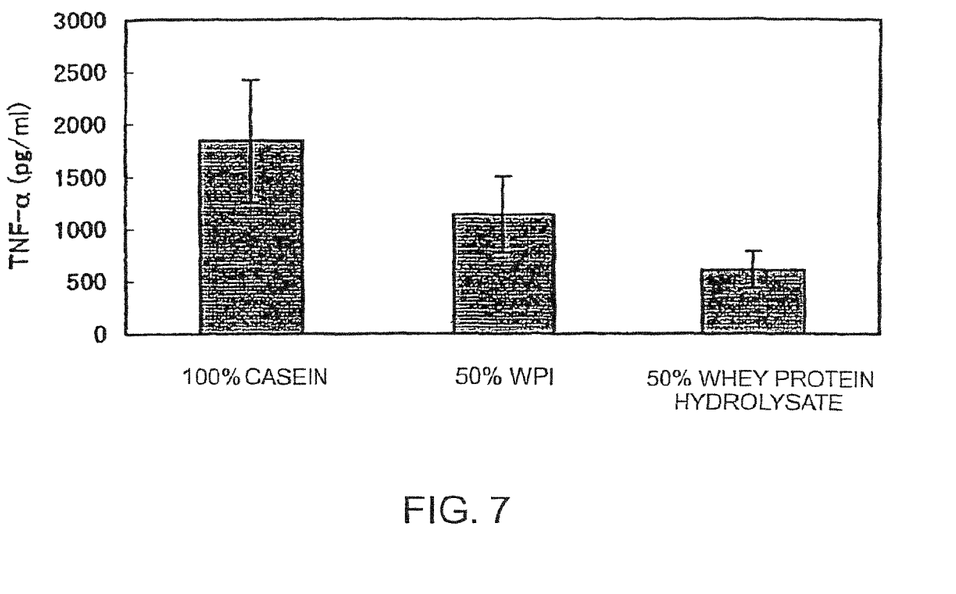
FIG. 7 shows the effect of the whey protein hydrolysate on the suppression of LPS-induced TNF-α production.

Compared to the casein group (the control group), the TNF-α production after LPS administration tended to be suppressed in the WPI group, whilst a significant suppression (p=0.033) was observed in the whey protein hydrolysate group (FIG. 7).

Figure 8:
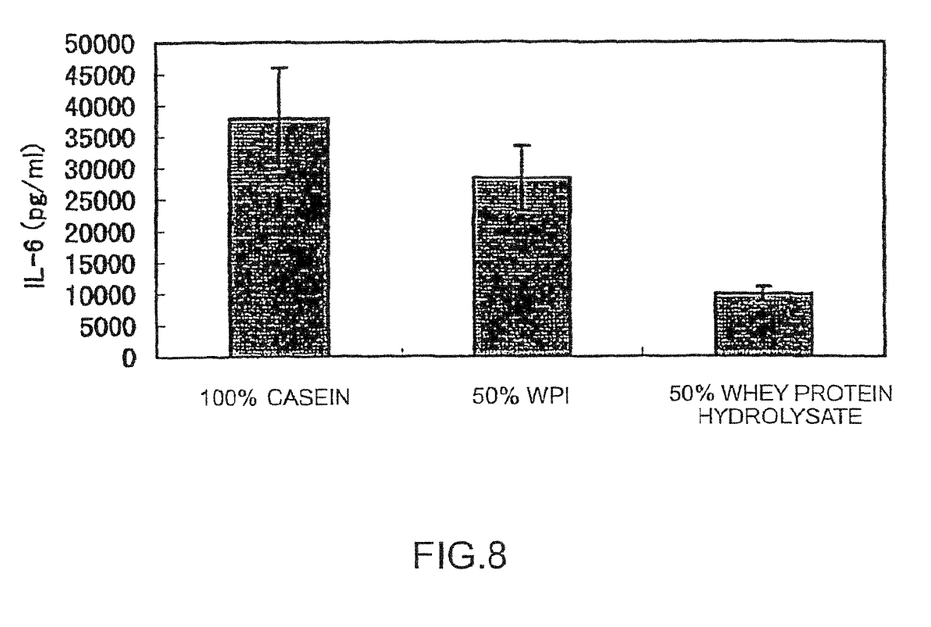
FIG. 8 shows the effect of the whey protein hydrolysate on the suppression of IL-6 production.

Compared to the casein group (the control group), the IL-6 production after LPS administration also tended to be suppressed in the WPI group whilst a significant suppression (p=0.0002) was seen in the whey protein hydrolysate group (FIG. 8).

The above-mentioned results showed that after oral ingestion of the whey protein hydrolysate, TNF-α and IL-6 production by LPS stimulation is significantly suppressed. Thus TNF-α production suppression was further investigated by varying the whey protein hydrolysate content.

Figure 9:
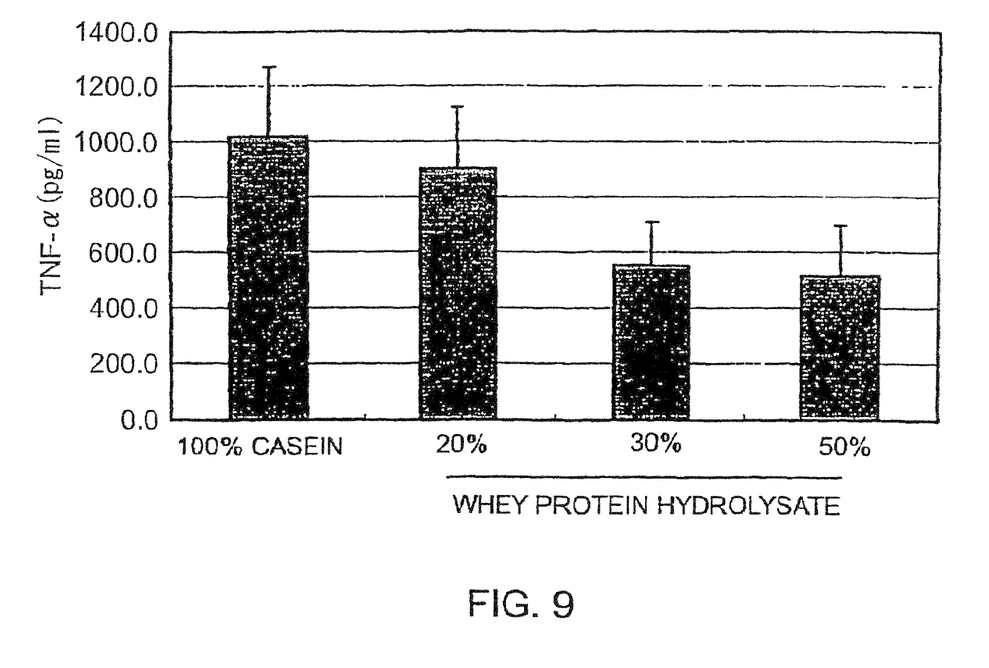
FIG. 9 shows the effect of whey protein hydrolysate dosage on the suppression of LPS-induced TNF-α production.

More specifically, similar experiments were performed on samples containing 100% casein, 80% casein+20% whey protein hydrolysate, 70% casein+30% whey protein hydrolysate, and 50% casein+50% whey protein hydrolysate as the protein source. After F-testing, Bonferroni/Dunn Tests were used to determine significant differences among the groups. These results are shown in FIG. 9.

TNF-α production after LPS administration tended to be suppressed in the 20% whey protein hydrolysate group when compared the casein group, and was significantly suppressed in the 30% and 50% whey protein hydrolysate groups (p=0.0496 and p=0.0479).

<Discussion>

1. Regarding the Relationship Between Liver Disease and TNF-α

During inflammation and immune reactions, TNF-α, IL-1, and IL-6 are produced mainly in macrophages and endothelial cells and function as pyrogens, as well as acting directly on hepatocytes to promote the production of acute phase proteins (C-reactive proteins; CRP) (Hepatology 23: 909-916, 1996; J. Immunol., 146: 3032-3037, 1991; Intensive Care Med., 24: 224-229, 1998; Hepatology 9: 497-499, 1989).

In acute hepatitis (especially fulminant hepatitis) and alcoholic liver damage, the involvement of inflammatory cytokines is indicated by fever, leukocytosis, CRP positivity, and such.

TNF-α is produced by macrophages following endotoxin stimulation, and may induce multiple organ failure ("Hepatic Failure-Fundamental and Clinical", Japan Medical Journal, Tokyo, 1994, pp. 30-46; "Hepatic Failure—Fundamental and Clinical", Japan Medical Journal, Tokyo, 1994, pp. 123-137). In fact, the function of the reticuloendothelial system declines in fulminant hepatitis patients, and successive occurrence of hyperendotoxinemia is often observed. Therefore production of TNF-α and IL-1 is considered to be facilitated in the body (Lancet, 2: 72-74, 1988). The concentrations of most inflammatory cytokines in the blood of fulminant hepatitis patients are significantly increased compared to acute hepatitis patients, and in particular, the concentrations of TNF-α and IL-6 correlate well with that of human hepatocyte growth factor (HGF), which is an indicator of liver regeneration (Clin. Exp. Immunol., 98: 71-77, 1994).

On the other hand, the concentration of inflammatory cytokines in the blood of patients with liver cirrhosis, which is a chronic liver disease, is significantly higher than in patients without liver cirrhosis. Regardless of the cause of the disease, this appears to reflect hepatic dysfunction rather than inflammation (Gastroenterology, 103: 264-274, 1992). In chronic type B hepatitis patients, IL-1 production is enhanced and correlates with the extent of hepatic fibrosis, and IL-1 is reported to be important in the progression to liver cirrhosis (Gastroenterology, 94: 999-1005, 1988).

Regarding the Relationship Between Liver Disease and IL-6

In alcoholic liver cirrhosis, increases in blood IL-6 levels and in IL-6 production in peripheral blood monocytes correlates positively with IgA levels, and negatively with IL-2 and IFN-γ production (Clin. Exp. Immunol., 77: 221-225, 1989). Blood IL-6 activity also increases during acute exacerbation of chronic hepatitis (Am. J. Gastroenterol., 86: 1804-1808, 1991). Blood IL-6 levels and IL-6 production by non-stimulated peripheral blood monocytes is thought to reflect the extent of individual liver inflammation.

In acute viral hepatitis, IL-6 is detected in sinusoidal endothelial cells, Kupffer cells, and invasive monocytes (J. Clin. Pathol., 45: 408-411, 1992). In chronic hepatitis, IL-6 is mainly detected in invasive lymphocytes and fibroblasts in the portal vein region. Therefore, in acute and chronic liver disease, IL-6 expression is predicted to be closely related to inflammation and immune response, regardless of the cause of the disease. IL-6 promotes the regeneration of hepatocytes, and its excessive production may induce tissue damage and fibrosis.

2. Nutrition Administration Route and Cytokine Production

To prevent metabolic and organ disorders caused by cytokines during invasive stress, it may be reasonable to induce normal production of cytokines locally while preventing them from spreading to the whole body. Therefore, differences in nutritional administration methods are being discussed with regards to the possibility of modifying cytokine production during invasive stress. In healthy adults who are not under invasive stress, administration of enteral nutrition or intravenous nutrition for one week does not cause an obvious difference in blood TNF and IL-6 levels (New Horizon, 2: 164-174, 1994). However, when endotoxin is injected intravenously seven days after providing enteral or intravenous nutrition to healthy adults, the resulting systemic biological reactions such as fever, and release of TNF and stressor hormones, are reported to be milder for enteral nutrition than for intravenous nutrition (Ann. Surg., 210: 449-457, 1989). Saito et al. have also used rats enterically administered with bacteria and subjected to different nutrition administration routes, to study the relationship between nutrition administration routes and cytokine production. This result confirms that modification of cytokine production by enteral nutrition as compared to intravenous nutrition is more favorable for biological reactions (Ann. Surg., 223: 84-93, 1996).

3. Regarding the Relationship Between Nutritional Compositions and Hepatopathy Suppressive Effect When the nutritional compositions of the present invention were orally ingested, increase of endotoxin-induced TNF-α and IL-6 concentrations in the blood were significantly suppressed. This suppressive effect is mainly due to the whey protein hydrolysates contained in the nutritional compositions. Suppression of the increase of blood TNF-α and IL-6 concentrations may be due to modifications to TNF-α and IL-6 production that occur due to oral ingestion of nutritional compositions.

INDUSTRIAL APPLICABILITY

The nutritional compositions of the present invention are useful for the nutritional management of acute hepatitis (fulminant hepatitis), chronic hepatitis, compensated cirrhosis, and decompensated cirrhosis. The present invention is particularly useful for nutritional management of chronic hepatic failure which has the possibility of developing into hepatic encephalopathy. In chronic hepatic failure, when food intake is possible, it is standard to restrict the amount of protein intake. However, when a high degree of protein restriction is continued for a prolonged period, appetite is inhibited, protein catabolism is promoted, and the poor nutritional condition is exacerbated. Therefore, some sort of nutritional supplementation becomes necessary. The food-type nutritional compositions of the present invention may improve the nutritional condition of chronic hepatic failure patients when supplemented with every meal.

Furthermore, the nutritional compositions of the present invention are useful for the nutritional management of patients under invasive stress due to surgery, infection, scalds, etc.

We claim:

1. A nutritional composition for liver disease patients who have not undergone surgery comprising:
   a) protein, wherein the protein comprises (i) a milk protein hydrolysate selected from the group consisting of whey protein hydrolysate, whey protein concentrate (WPC) hydrolysate, and whey protein isolate (WPI) hydrolysate in an amount of 0.9 to 3 g per 100 mL of the composition and (ii) protein derived from fermented milk in an amount of 2.5 to 4.5 g per 100 mL of the composition;
   b) lipids, wherein the lipids comprise an oleic acid-containing oil and lecithin, wherein the lecithin is milk lecithin or soybean lecithin, or both; and
   c) carbohydrate, wherein the carbohydrate comprises palatinose in an amount of 4 to 15 g per 100 mL of the composition.

2. The nutritional composition according to claim 1, wherein said fermented milk-derived protein is from a composition wherein whey in the fermented milk has been reduced.

3. The nutritional composition according to claim 1, wherein said fermented milk-derived protein is from fresh cheese.

4. The nutritional composition according to claim 3, wherein said fresh cheese is quark.

5. A nutritional composition for liver disease patients and/or patients under high levels of invasive stress whose concentration of inflammatory cytokines in blood is at a predetermined concentration or more, wherein said nutritional composition comprises:
   a) protein, wherein the protein comprises (i) a milk protein hydrolysate selected from the group consisting of whey protein hydrolysate, whey protein concentrate (WPC) hydrolysate, and whey protein isolate (WPI) hydrolysate in an amount of 0.9 to 3 g per 100 mL of the composition and (ii) protein derived from fermented milk in an amount of 2.5 to 4.5 g per 100 mL of the composition;
   b) lipids, wherein the lipids comprise an oleic acid-containing oil and lecithin, wherein the lecithin is milk lecithin or soybean lecithin, or both; and
   c) carbohydrate, wherein the carbohydrate comprises palatinose in an amount of 4 to 15 g per 100 mL of the composition.

6. The nutritional composition according to claim 5, wherein said fermented milk-derived protein is from a composition in which the whey in the fermented milk has been reduced.

7. The nutritional composition according to claim 5, wherein said fermented milk-derived protein is from fresh cheese.

8. The nutritional composition according to claim 7, wherein said fresh cheese is quark.

9. A method for providing nutrition to a liver disease patient, a liver disease patient who has not undergone surgery and/or a patient under high level of invasive stress whose concentration of inflammatory cytokines in blood is at a predetermined concentration or more, wherein said method comprises administering to such a patients an effective amount of the nutritional composition as set forth in claim 1.

10. The method of claim 9, wherein the patient has liver cirrhosis.

11. The method of claim 9, wherein the patient has hepatic failure.

12. The method, according to claim 9, wherein said fermented milk-derived protein is from a composition wherein whey in the fermented milk has been reduced.

13. The method, according to claim 9, wherein said fermented milk-derived protein is from fresh cheese.

14. The method, according to claim 13, wherein said fresh cheese is quark.

15. A method for providing nutrition to a liver disease patient who has not undergone surgery and/or a patient under high level of invasive stress whose concentration of inflammatory cytokines in blood is at a predetermined concentration or more, wherein said method comprises administering to such a patient an effective amount of the nutritional composition as set forth in claim 5.

16. The method, according to claim 15, wherein said fermented milk-derived protein is from a composition wherein whey in the fermented milk has been reduced.

17. The method, according to claim 15, wherein said fermented milk-derived protein is from fresh cheese.

18. The method, according to claim 17, wherein said fresh cheese is quark.

* * * * *